United States Patent
Wood

(10) Patent No.: US 6,812,374 B1
(45) Date of Patent: Nov. 2, 2004

(54) MODIFIED ADHESIVE GAUZE

(76) Inventor: Arlene G. Wood, 1110 Woodcrest Ave., Clearwater, FL (US) 33756

(*) Notice: Subject to any disclaimer, the term of this patent is extended or adjusted under 35 U.S.C. 154(b) by 83 days.

(21) Appl. No.: 10/159,049

(22) Filed: May 31, 2002

(51) Int. Cl.[7] .............................. A61F 5/00; A61F 13/00
(52) U.S. Cl. ......................................... 602/41; 128/888
(58) Field of Search ............. 602/41–59; 604/305–308; 128/888, 889

(56) References Cited

U.S. PATENT DOCUMENTS

| | | | |
|---|---|---|---|
| 1,920,808 A | | 8/1933 | Sander |
| 4,212,296 A | * | 7/1980 | Schaar ........................ 602/42 |
| 4,423,101 A | * | 12/1983 | Willstead ..................... 428/76 |
| 4,726,364 A | | 2/1988 | Wylan |
| 5,267,952 A | | 12/1993 | Gardner |
| 5,336,209 A | | 8/1994 | Porzilli |
| 5,423,736 A | * | 6/1995 | Cartmell et al. .............. 602/42 |
| 5,538,500 A | * | 7/1996 | Peterson ...................... 602/48 |
| 5,571,079 A | * | 11/1996 | Bello et al. .................. 602/46 |
| D424,699 S | | 5/2000 | Allen |
| 6,107,536 A | | 8/2000 | Dadinis |

* cited by examiner

Primary Examiner—John J. Calvert
Assistant Examiner—Linh Truong

(57) ABSTRACT

A modified adhesive gauze for absorbing discharge from wounds in an adhesive bandage package. The modified adhesive gauze includes a structural membrane that supports a thick dome shaped gauze pad and a plurality of adhesive strips to hold the gauze in place. The gauze pad has an increased capacity to contain matter discharged from the wound and would therefore require less changing while still providing protection for the wound.

16 Claims, 2 Drawing Sheets

MODIFIED ADHESIVE GAUZE

BACKGROUND OF THE INVENTION

1. Field of the Invention

The present invention relates to bandages and more particularly pertains to a new modified adhesive gauze for absorbing excess discharge from wounds in an adhesive bandage package.

2. Description of the Prior Art

The use of bandages is known in the prior art. More specifically, bandages heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,726,364 which teaches a method of retaining a gauze pad on an adhesive bandage. The patent does not teach a thick dome shaped gauze pad or the placement of the adhesive in strips.

U.S. Pat. No. 5,267,952 teaches a gauze pad mounted on an elastic limb sleeve to control swelling. The patent does not teach a thick dome shaped gauze pad or the placement of the adhesive in strips.

U.S. Pat. No. 5,336,209 teaches a bandage with a nonstick surface between the gauze pad and the wound site to minimize damage caused when removing the bandage. The patent does not teach a thick dome shaped gauze pad or the placement of the adhesive in strips.

U.S. Pat. No. 6,107,536 teaches a bandage support membrane with flexible pleats or articulations for use on joints or flexible areas. The patent does not teach a thick dome shaped gauze pad or the placement of the adhesive in strips.

U.S. Design Pat. No. Des. 424,699 teaches an ornamental design for an adhesive bandage. The patent does not teach a thick dome shaped gauze pad or the placement of the adhesive in strips.

While these devices fulfill their respective, particular objectives and requirements, the aforementioned patents do not disclose a new modified adhesive gauze. The inventive device includes a structural membrane that supports a thick dome shaped gauze pad and a plurality of adhesive strips to hold the gauze in place.

In these respects, the modified adhesive gauze according to the present invention substantially departs from the conventional concepts and designs of the prior art, and in so doing provides an apparatus primarily developed for the purpose of absorbing excess discharge from wounds in an adhesive bandage package.

SUMMARY OF THE INVENTION

In view of the foregoing disadvantages inherent in the known types of bandages now present in the prior art, the present invention provides a new modified adhesive gauze construction wherein the same can be utilized for absorbing excess discharge from wounds in an adhesive bandage package.

The general purpose of the present invention, which will be described subsequently in greater detail, is to provide a new modified adhesive gauze apparatus and method which has many of the advantages of the bandages mentioned heretofore and many novel features that result in a new modified adhesive gauze which is not anticipated, rendered obvious, suggested, or even implied by any of the prior art bandages, either alone or in any combination thereof.

To attain this, the present invention generally comprises a structural membrane that supports a thick dome shaped gauze pad and a plurality of adhesive strips to hold the gauze in place.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new modified adhesive gauze apparatus and method which has many of the advantages of the bandages mentioned heretofore and many novel features that result in a new modified adhesive gauze which is not anticipated, rendered obvious, suggested, or even implied by any of the prior art bandages, either alone or in any combination thereof.

It is another object of the present invention to provide a new modified adhesive gauze, which may be easily and efficiently manufactured and marketed.

It is a further object of the present invention to provide a new modified adhesive gauze, which is of a durable and reliable construction.

An even further object of the present invention is to provide a new modified adhesive gauze which is susceptible of a low cost of manufacture with regard to both materials and labor, and which accordingly is then susceptible of low prices of sale to the consuming public, thereby making such modified adhesive gauze economically available to the buying public.

Still yet another object of the present invention is to provide a new modified adhesive gauze, which provides in the apparatuses and methods of the prior art some of the advantages thereof, while simultaneously overcoming some of the disadvantages normally associated therewith.

Still another object of the present invention is to provide a new modified adhesive gauze for absorbing excess discharge from wounds in an adhesive bandage package.

Yet another object of the present invention is to provide a new modified adhesive gauze which includes a structural membrane that supports a thick dome shaped gauze pad and a plurality of adhesive strips to hold the gauze in place.

Still yet another object of the present invention is to provide a new modified adhesive gauze that reduces the possibility or the extent of damage incurred when the bandage is removed from a wound.

Even still another object of the present invention is to provide a new modified adhesive gauze that reduces the possibility of infection in the wound the bandage is use on.

These together with other objects of the invention, along with the various features of novelty, which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
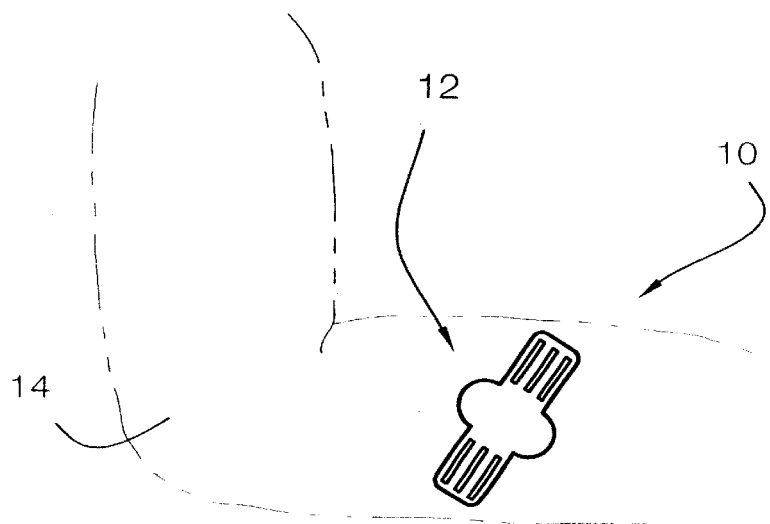
FIG. 1 is a schematic view of a new modified adhesive gauze according to the present invention.

With reference now to the drawings, and in particular to FIGS. 1 through 4 thereof, a new embodying the principles and concepts of the present invention and generally designated by the reference numeral 10 will be described.

As best illustrated in FIGS. 1 through 4, the modified adhesive gauze 10 generally comprises a support membrane 20 that possesses a gauze pad 40 and anchoring portions 24 with adhesive strips.

The support membrane 20 may comprise a covering that holds the gauze pad 40. The support membrane 20 may include a deformation or indentation to hold the gauze pad 40 in place. The deformation or gauze receptacle 22 of the support membrane 20 would correspond to the shape of the gauze pad 40.

Figure 2:
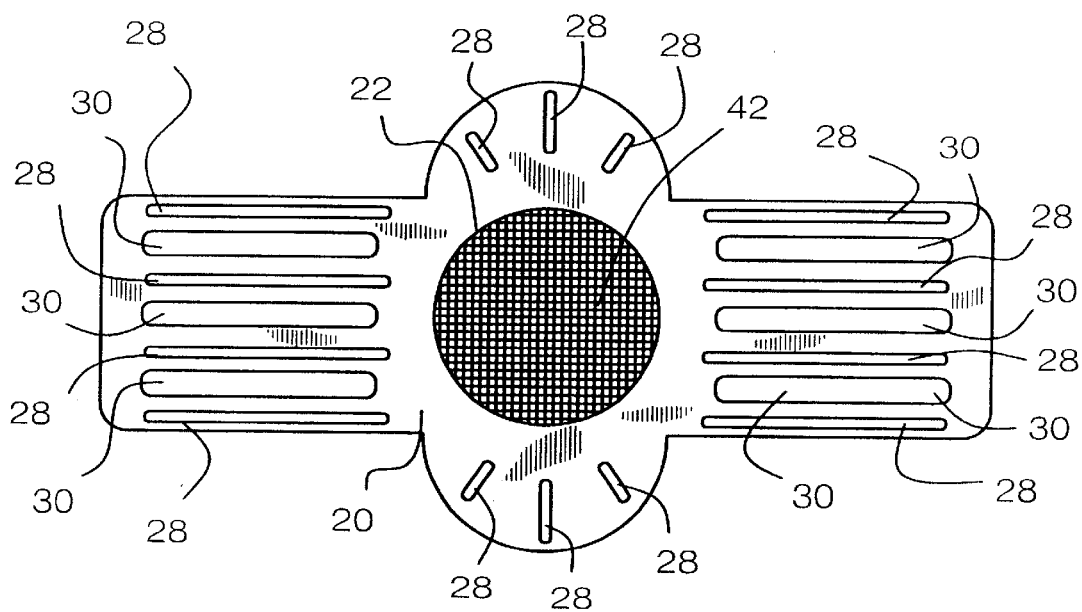
FIG. 2 is a bottom view of the present invention showing the gauze pad.
Figure 3:
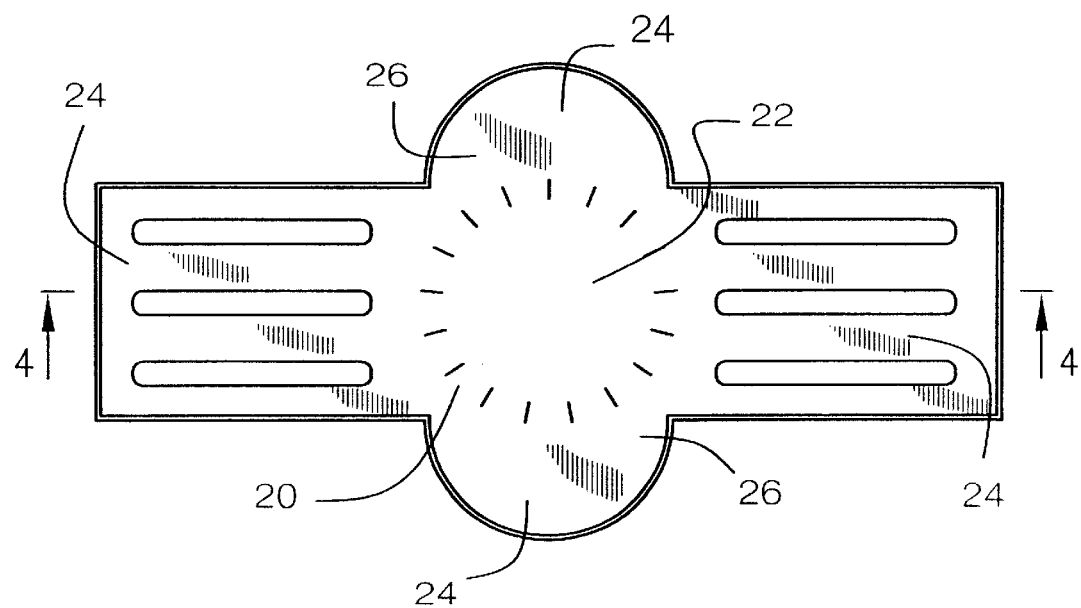
FIG. 3 is a top view of the present invention.
Figure 4:
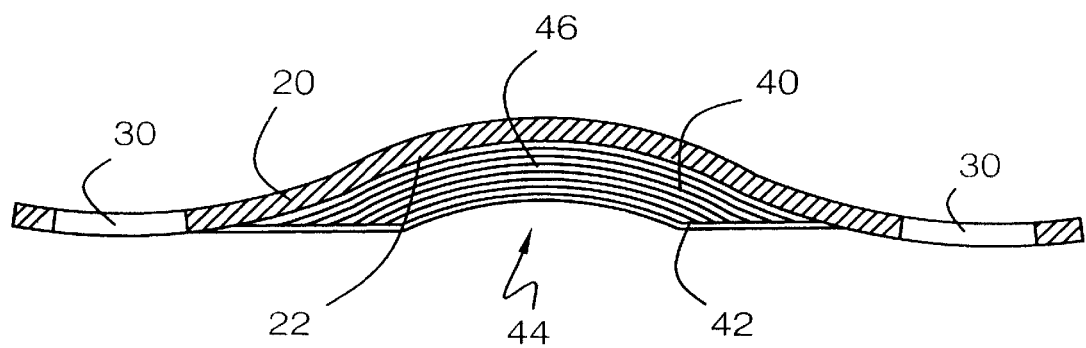
FIG. 4 is a cross sectional view of the present invention.

The support membrane 20 may comprise a variety of shapes. The most common shape in the industry is an elongated strip wherein the gauze pad 30 is held in between two anchoring portions 24. A support membrane 20 with anchoring portions 24 formed into an elongated strip may include supplementary anchoring portions 24. These supplementary anchoring portions 24 may be in the form of additional similar anchoring portions 24 radiating from the central gauze pad to form a cross. Theses supplementary anchoring portions may be truncated to form wings 26. FIG. 2 illustrates such a configuration with two anchoring portions 24 located to the left and right of the gauze pad 40 and supplementary wings 26 located above and below the gauze pad 40.

The support membrane 20 may be constructed from a variety of fabric or plastic materials. The support membrane may be flexible to move with the surrounding surface area of the skin near the wound site 12. The support membrane 20 may also be porous to allow the circulation of air and the evaporation of perspiration from the area surrounding the wound site 12. The portals for the circulation of air may be in the form of perforations as is generally practiced in the field of adhesive bandages. Optionally the circulation portals may take the form of elongated slits 30.

The support membrane 20 may be held to the wound site 12 with adhesive. The adhesive would be located on the anchoring portions 24 of the support membrane 20. The adhesive may be situated on the anchoring portion 24 in a variety of configurations. To reduce the potential for damaging the area surrounding the wound site 12, the adhesive may be arranged in narrow strips 28. The adhesive strips 28 may allow adequate adhesion to retain the support membrane to the area surrounding the wound site 12 while allowing sufficient circulation to the user's skin. The adhesive strips may also minimize the pain and/or damage associated with removal of adhesive bandages due to the reduced surface area of the skin that the adhesive is contacting.

The gauze pad 40 of the modified adhesive gauze 10 may be composed of an absorbent fibrous or layered material 46 designed to capture fluids or viscous liquids. The absorbent material 46 may contain moisture capturing powders or gels. The absorbent material 46 may also contain antiseptic or antibiotic material included in its composition. The gauze pad would be held on one side within the gauze receptacle 22 of the support membrane 20. On the side to be applied to the wound, the gauze pad 40 may be retained by a retention mesh 42. The retention mesh 42 may form a porous yet non-stick barrier which prevents the cross coagulation of fluids or epitheliazation, which would tend to fix the absorbent material to the wound. The retention mesh 42 may comprise a non-stick material such as TEFLA by Kendall Company Ltd., Melolin or Opsite by Smith and Nephew Medical Ltd., or Tegaderm by the 3M Corp. that would provide a relatively non-stick barrier between absorbent material and the wound.

The gauze pad 40 may be thicker than existing adhesive bandages. The increased volume of gauze padding may allow the gauze pad 40 to absorb fluids discharged from a wound. Certain wounds, for example burns or infected skin ruptures, tend to weep or discharge fluids or viscous matter that the gauze in an adhesive bandage cannot absorb. The overtaxing of the gauze may force the matter to leak out of the perforations in the bandage. This leaking of matter causes an non-hygienic situation that may lead to infection of the wound. The gauze pad 40 of the modified adhesive gauze 10 therefore may be exceptionally thick. To make the most efficient use of space within the supporting membrane, the gauze pad may conform to a convex or domal shape. The convex shape of the gauze pad 40 may allow the absorption of fluids in all directions. This may maximize the surface tension or capillary draw of the absorbent material 46.

The gauze pad 40 may include a concave cavity 44 on the wound 12 side of the gauze to reduce pressure on the wound site 12. Similar to the design of bunion pads the gauze pad 40 may allow a space between the pad and the wound to minimize any pain associated with pressure on the wound site 12.

In use, the modified adhesive pad 10 would be applied to a wound site 12 by placing the center of the gauze pad 40 directly over the wound 12. The gauze would be held in place by a support membrane 20. The support membrane 20 would hold the gauze pad 40 in a gauze receptacle 22. The support membrane 20 would be attached to the area surrounding the wound site 12 by adhesive strips 28 arranged on the anchoring portions 24 of the support membrane 20. The adhesive strips 28 may include circulation slits 30 to allow the circulation of air to and from the user's skin as is necessary for perspiration. The gauze pad 40 is retained in the support membrane 20 by a retention mesh 42. The retention mesh also may serve to separate the wound from the absorbent material 46.

If the wound should discharge fluids or viscous liquids, the absorbent material 46 of the gauze pad 40 may absorb them. The capacity of the gauze pad 40 may be adequate to absorb a substantial amount without compromising the effectiveness of the protective qualities associated with bandages. The ability to absorb a great quantity of matter may also decrease the number of changings the wound dressing may have to undergo. Thus, the modified adhesive gauze 10 may impose less pain and suffering on its user.

When removing the modified adhesive gauze 10, the anchoring portions 24 may be lifted from the area surrounding the wound site 12. Due to the reduced surface area the adhesive occupies on the anchoring portions 24, it is easier to remove the support membrane 20 in comparison to anchoring portions on which adhesive is applied to the entire surface of the anchoring portion. Once removed, the absorbent qualities of the absorbent material 46 would retain any discharged matter within the gauze pad until disposed.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A bandage with increased capacity to absorb wound discharge, the bandage comprising:
   a gauze pad for absorbing wound discharge; and
   a support membrane for mounting the gauze pad to the skin of a user, the membrane comprising:
      an anchoring portion to provide a structure to hold the gauze pad to the wound, the anchoring portion including adhesive on a surface area of the anchoring portion to adhere the anchoring portion to the skin of the user;
      a gauze receptacle for receiving the gauze pad; and
      circulation ports through the support membrane to allow air to circulate to and from the area of skin surrounding the wound site; wherein the gauze pad comprises:
      absorbent material to draw wound discharge from the wound and into the gauze pad; and
      a retention mesh is coupled to the support membrane such that the gauze pad is positioned between the retention mesh and the support membrane, the retention mesh retains the absorbent gauze pad in the gauze receptacle and separates the wound from the absorbent material, the retention mesh is permeable such that the retention mesh is adapted for permitting fluids from the wound to be absorbed by the absorbent material, the retention mesh comprises an arcuate portion such that the arcuate portion pushes the gauze pad into the gauze receptacle to separate the gauze pad from the wound and inhibit the gauze pad from becoming coagulated to the wound.

2. The bandage of claim 1 wherein support membrane comprises an elongated band.

3. The bandage of claim 2 wherein the anchoring portions are disposed to two opposite sides of the gauze pad such that the gauze pad is a centrally located therebetween.

4. The bandage of claim 3 wherein the support membrane includes supplementary anchoring portions.

5. The bandage of claim 4 wherein the supplementary portions comprise wings.

6. The bandage of claim 1 wherein the adhesive is applied to only a portion of the surface area of the anchoring portion.

7. The bandage of claim 6 wherein the adhesive is arranged in strips.

8. The bandage of claim 7 wherein the adhesive strips extend outwardly from a centrally located gauze pad.

9. The bandage of claim 1 wherein the gauze receptacle conforms to the shape of the gauze pad.

10. The bandage of claim 1 wherein the circulation ports comprise elongated slits.

11. The bandage of claim 1 wherein the gauze pad has a convex shape.

12. The bandage of claim 11 wherein the convex shaped gauze pad forms a concave cavity forming a dome.

13. The bandage of claim 1 wherein the absorbent material has a moisture-capturing substance applied thereto.

14. The bandage of claim 1 wherein the absorbent material has an antiseptic substance applied thereto.

15. The bandage of claim 1 wherein the absorbent material has an antibiotic substance applied thereto.

16. A bandage with increased capacity to absorb wound discharge, the bandage comprising:
   a gauze pad for absorbing wound discharge; and
   a support membrane for mounting the gauze pad to the skin of a user, the membrane comprising:
      an anchoring portion to provide a structure to hold the gauze pad to the wound, the anchoring portion including adhesive on a surface area of the anchoring portion to adhere the anchoring portion to the skin of the user;
      a gauze receptacle for receiving the gauze pad; and
      circulation ports through the support membrane to allow air to circulate to and from the area of skin surrounding the wound site; wherein the gauze pad comprises:
      absorbent material to draw wound discharge from the wound and into the gauze pad; and
      a retention mesh is coupled to the support membrane such that the gauze pad is positioned between the retention mesh and the support membrane, the retention mesh that retains the absorbent gauze pad in the gauze receptacle and separates the wound from the absorbent material, the retention mesh is permeable such that the retention mesh is adapted for permitting fluids from the wound to be absorbed by the absorbent material, the retention mesh comprises an arcuate portion such that the arcuate portion pushes the gauze pad into the gauze receptacle to separate the gauze pad from the wound and inhibit the gauze pad from becoming coagulated to the wound;

wherein support membrane comprises an elongated band;

wherein the anchoring portions are disposed to two opposite sides of the gauze pad such that the gauze pad is a centrally located therebetween;

wherein the support membrane includes supplementary anchoring portions;

wherein the supplementary portions comprise wings;

wherein the adhesive is applied to only a portion of the surface area of the anchoring portion, the adhesive being arranged in strips, the adhesive strips extending outwardly from a centrally located gauze pad;

wherein the gauze receptacle conforms to the shape of the gauze pad;

wherein the circulation ports comprise elongated slits;

wherein the gauze pad has a convex shape defining a concave cavity forming a dome;

wherein the absorbent material has a moisture-capturing substance applied thereto;

wherein the absorbent material has an antiseptic substance applied thereto; and wherein the absorbent material has an antibiotic substance applied thereto.

* * * * *